United States Patent [19]

Hauptmann et al.

[11] 4,051,952
[45] Oct. 4, 1977

[54] FISH CHARACTERISTIC DETECTING AND SORTING APPARATUS

[75] Inventors: Edward G. Hauptmann; John Richard Green, both of West Vancouver, Canada

[73] Assignee: Neptune Dynamics Ltd., North Vancouver, Canada

[21] Appl. No.: 610,661

[22] Filed: Sept. 5, 1975

[30] Foreign Application Priority Data

Sept. 9, 1974   Canada ................................... 208741

[51] Int. Cl.² ............................................. B07C 5/34
[52] U.S. Cl. ................................. 209/73; 209/74 M; 209/111.5; 209.126; 209/1116; 198/741; 198/415
[58] Field of Search .............. 209/111.6, 111.7, 111.5, 209/73, 126; 250/451, 221, 456; 198/268–271, 283, 287, 218, 223, 224; 356/41; 294/3, 28

[56] References Cited

U.S. PATENT DOCUMENTS

| | | | |
|---|---|---|---|
| 1,430,011 | 9/1922 | Heath | 198/271 |
| 1,649,304 | 11/1927 | Gray | 198/269 |
| 3,152,587 | 10/1964 | Ullrich et al. | 356/41 X |
| 3,499,527 | 3/1970 | Badgley | 209/111.6 |
| 3,603,457 | 9/1971 | Flodin | 209/111.7 |
| 3,859,522 | 1/1975 | Cuthbert | 209/111.7 |
| 3,930,994 | 1/1976 | Conway | 209/111.5 |

Primary Examiner—Allen N. Knowles
Attorney, Agent, or Firm—Robert W. Beach

[57] ABSTRACT

Fish are oriented by laying them in random arrangement in the central portion of a vibrating trough, the opposite ends of which form passages slightly wider than the widest fish being sorted. Fish move headfirst toward the trough ends, and the movement of fish discharged in single file from such trough ends is accelerated to propel fish past detector means. Such detector means include a radiant-energy source and fish-sorting means responsive to energy from such source operable to deflect fish leaving such source for channeling the fish corresponding to a characteristic detected by the detector. Such characteristic may be sex, length or sidewise orientation. Alternatively, fish can be subjected to detector means for energizing a signal simply to indicate a characteristic of the fish without sorting the fish, such as by placing a fish on an energy-transmitting surface, applying an energy-responsive element to the opposite side of the fish and actuating a signal in response to operation of the energy-responsive element.

18 Claims, 33 Drawing Figures

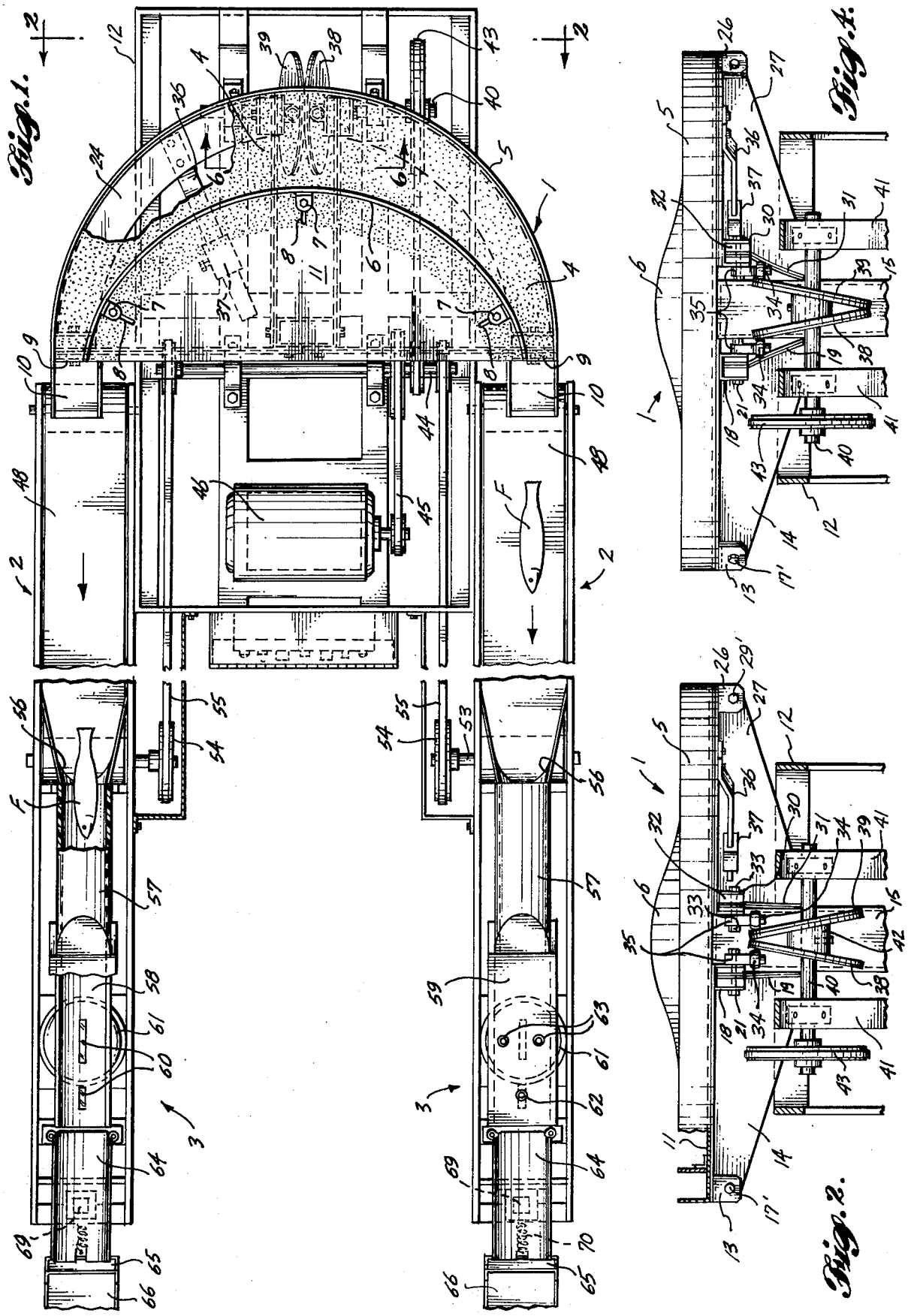

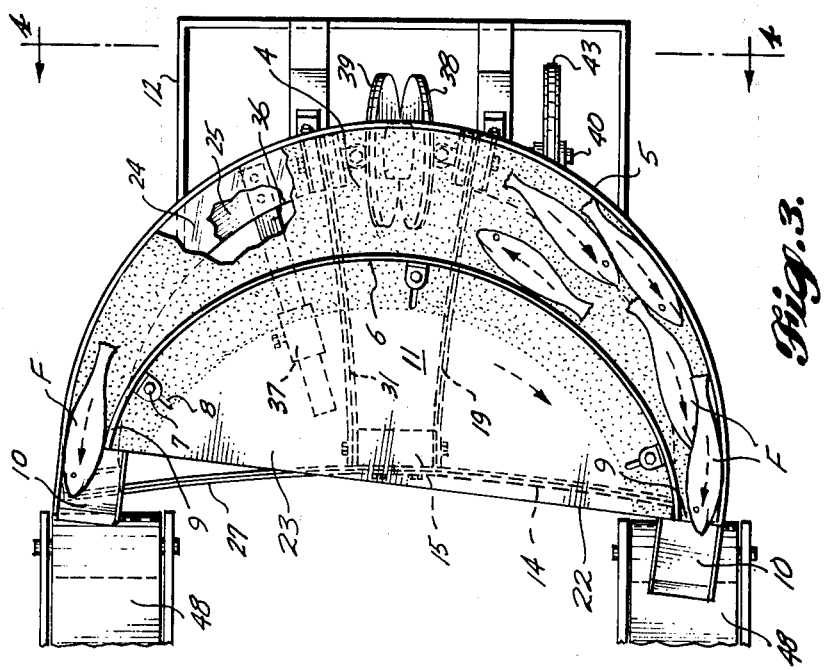
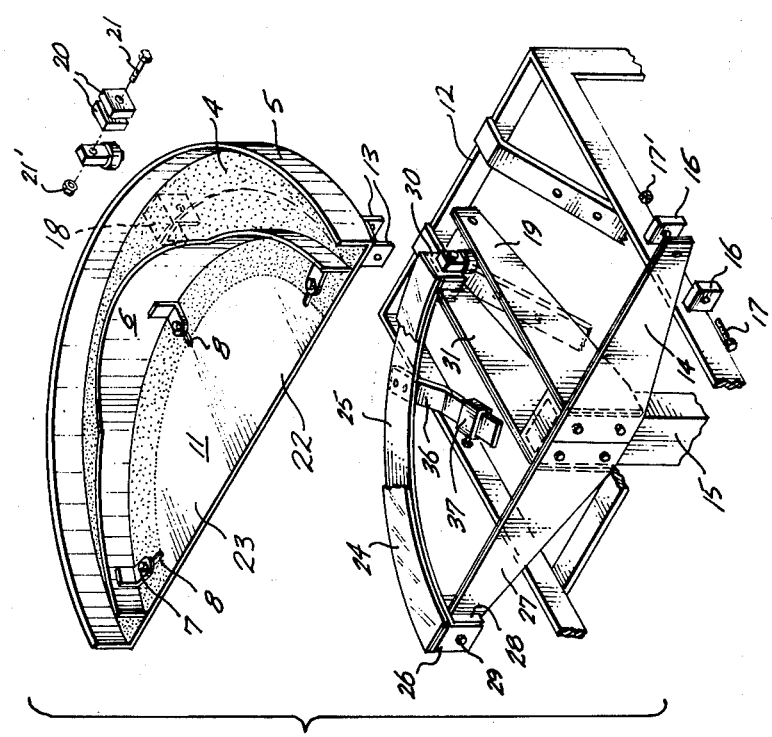
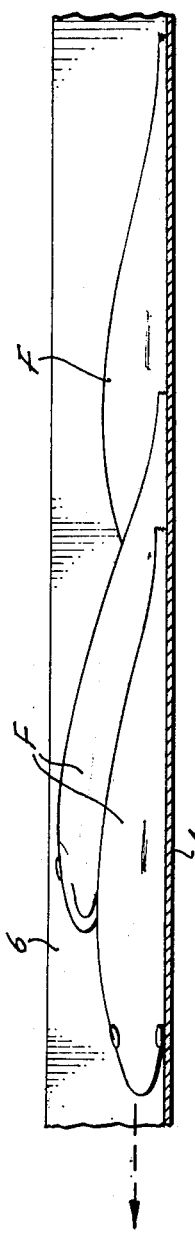

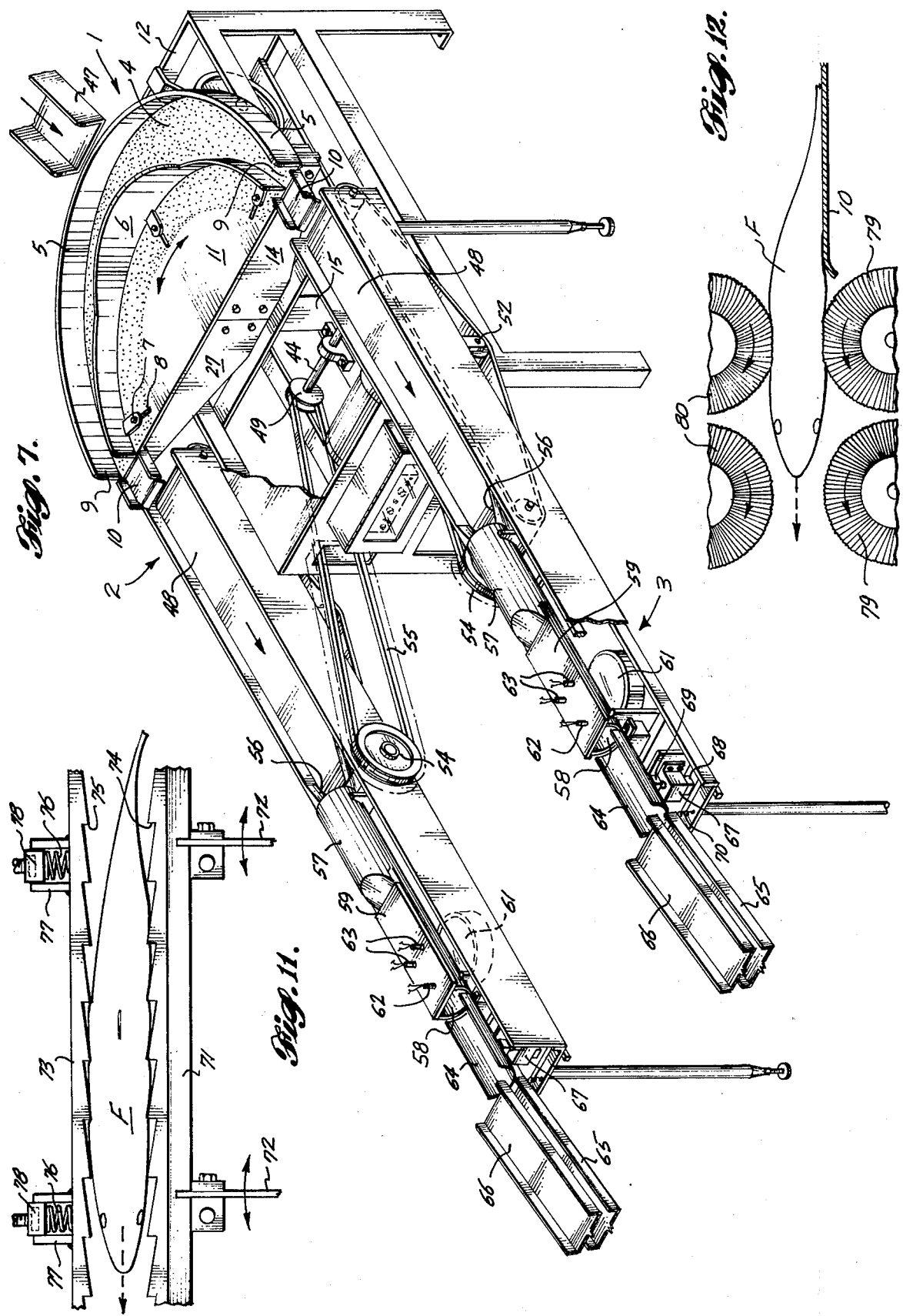

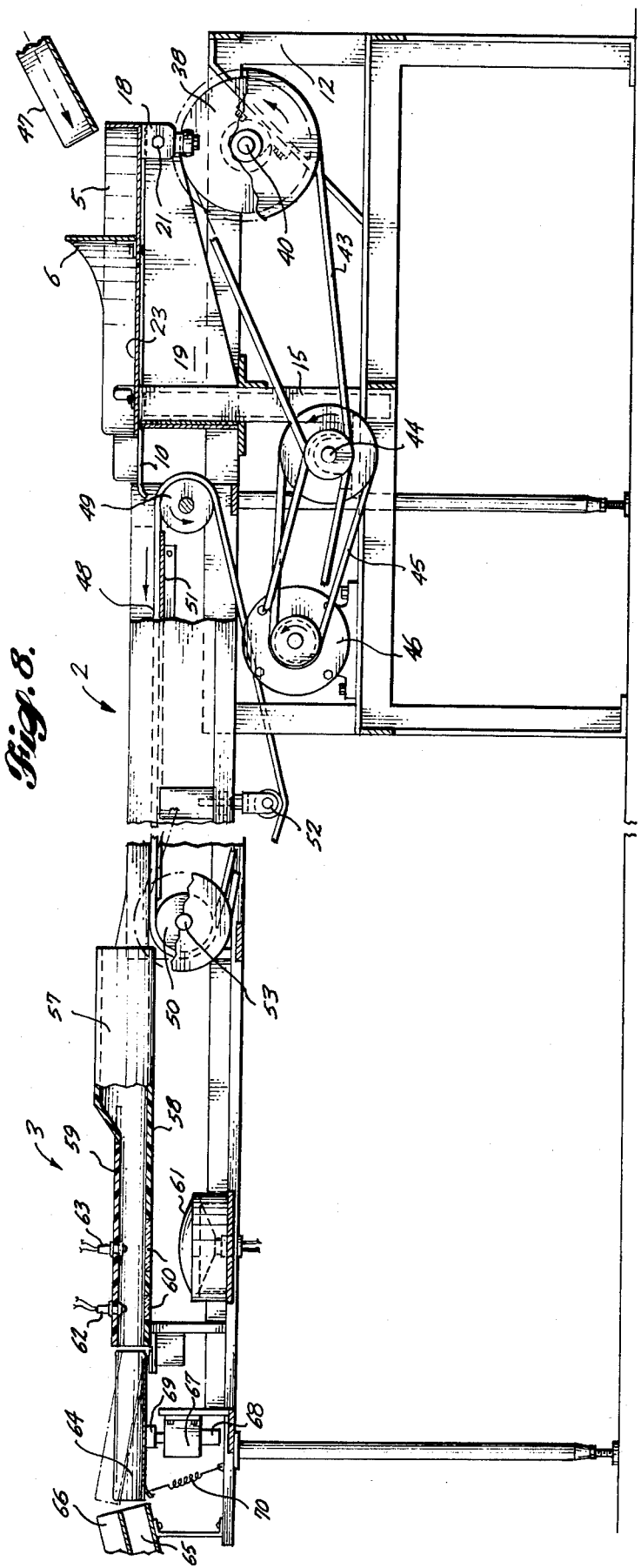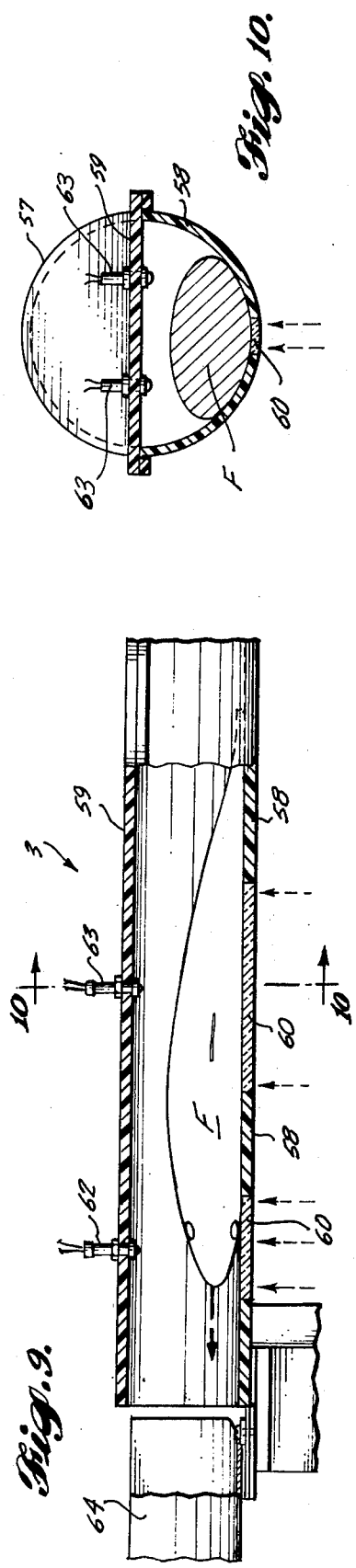

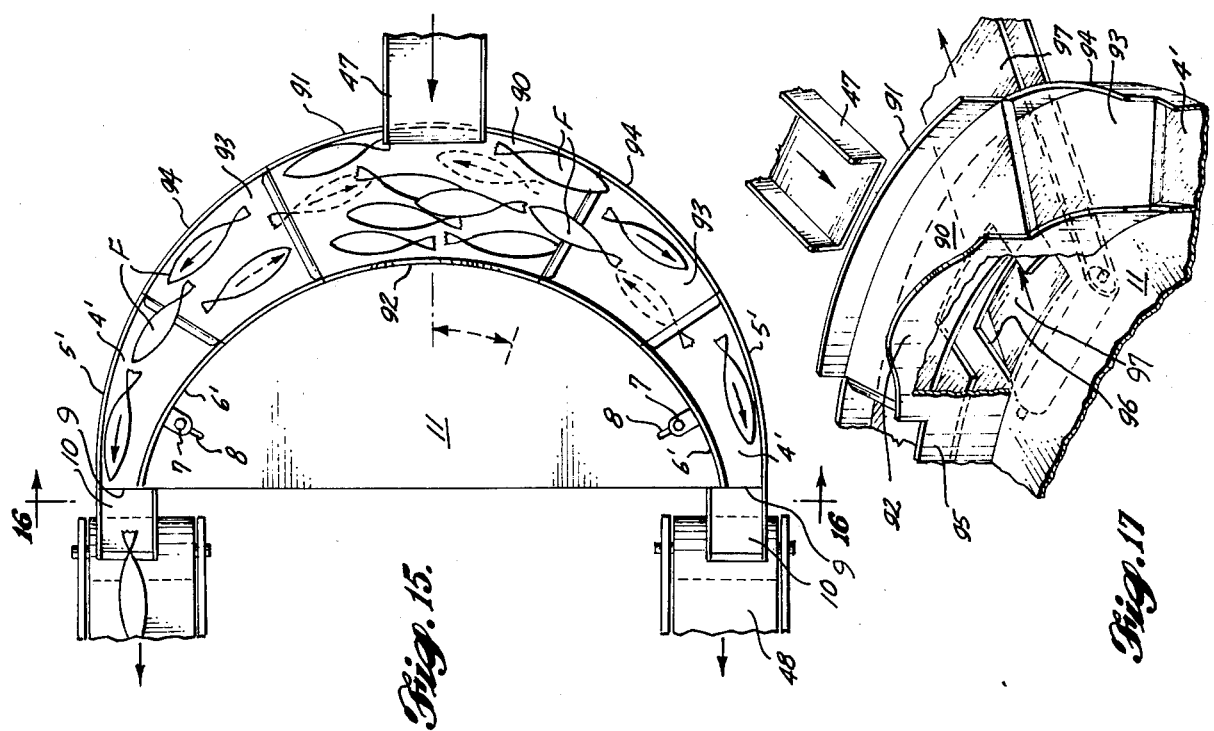
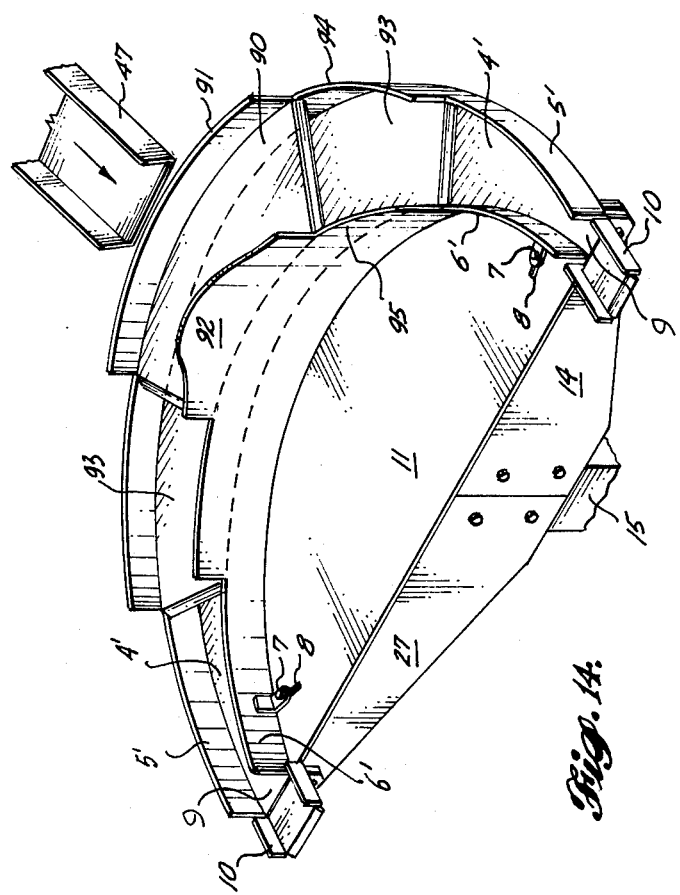
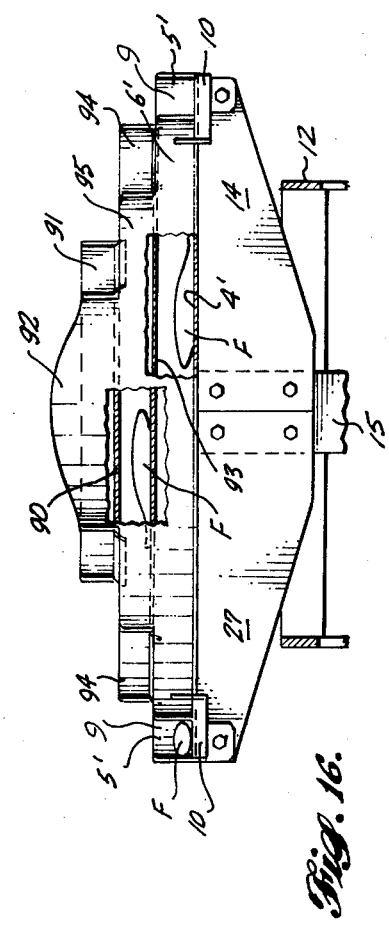

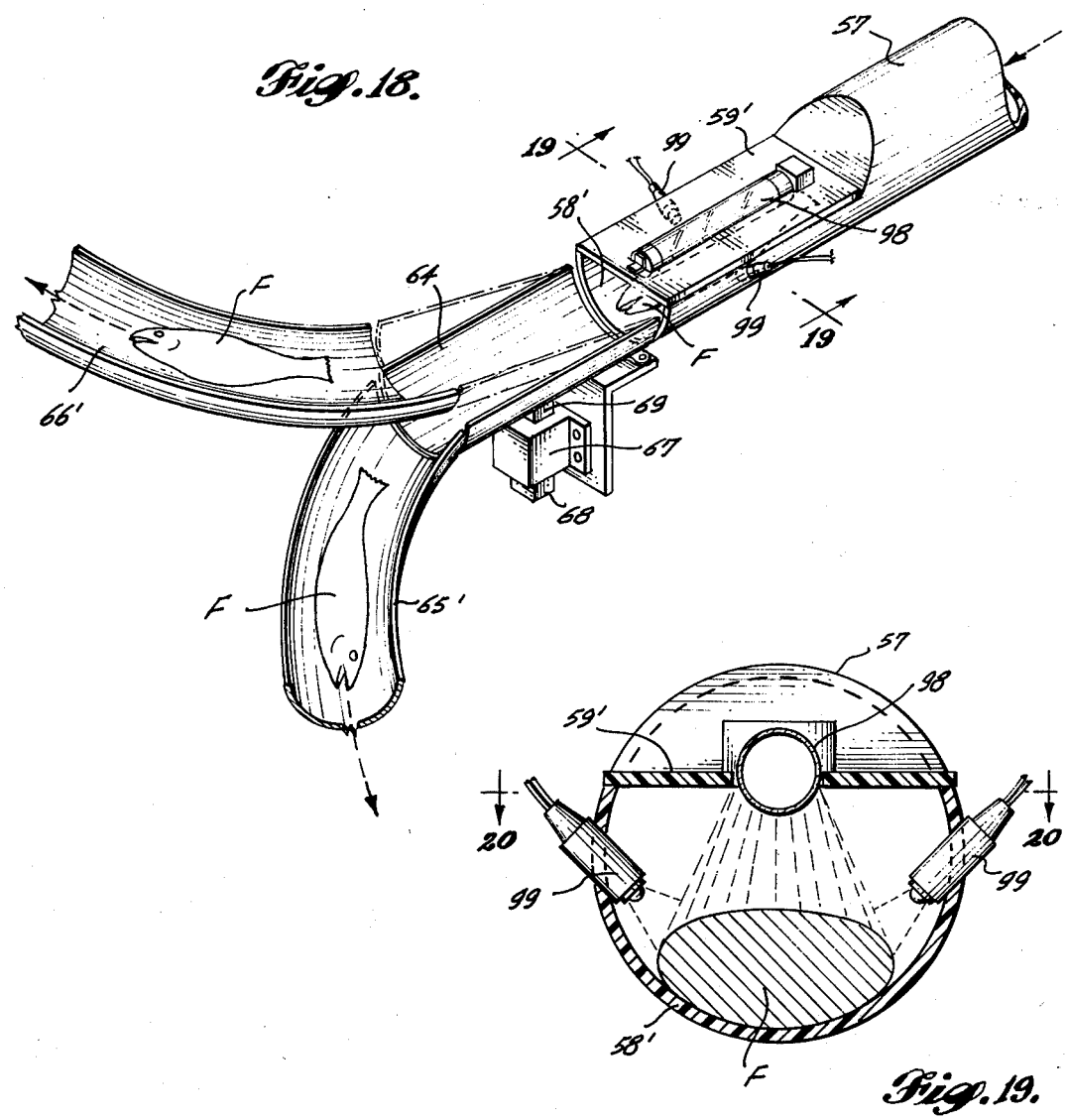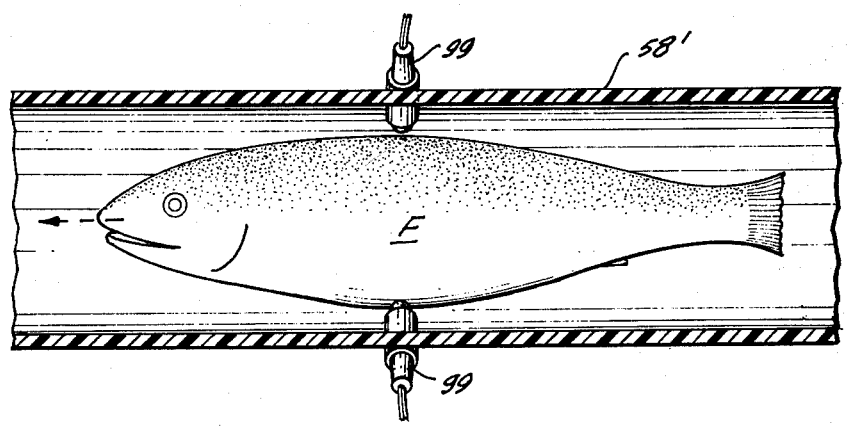

RADIANT ENERGY SOURCE

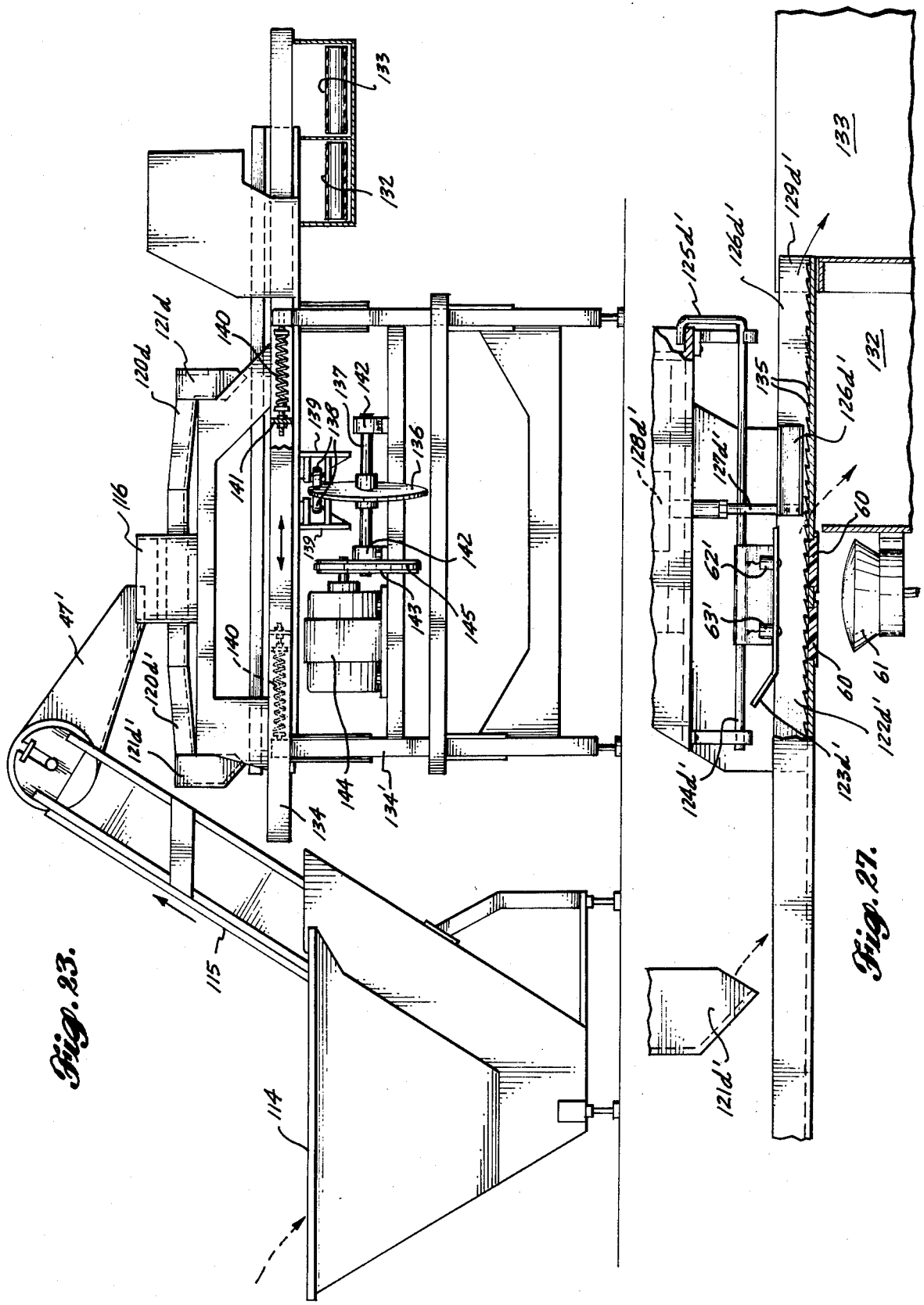

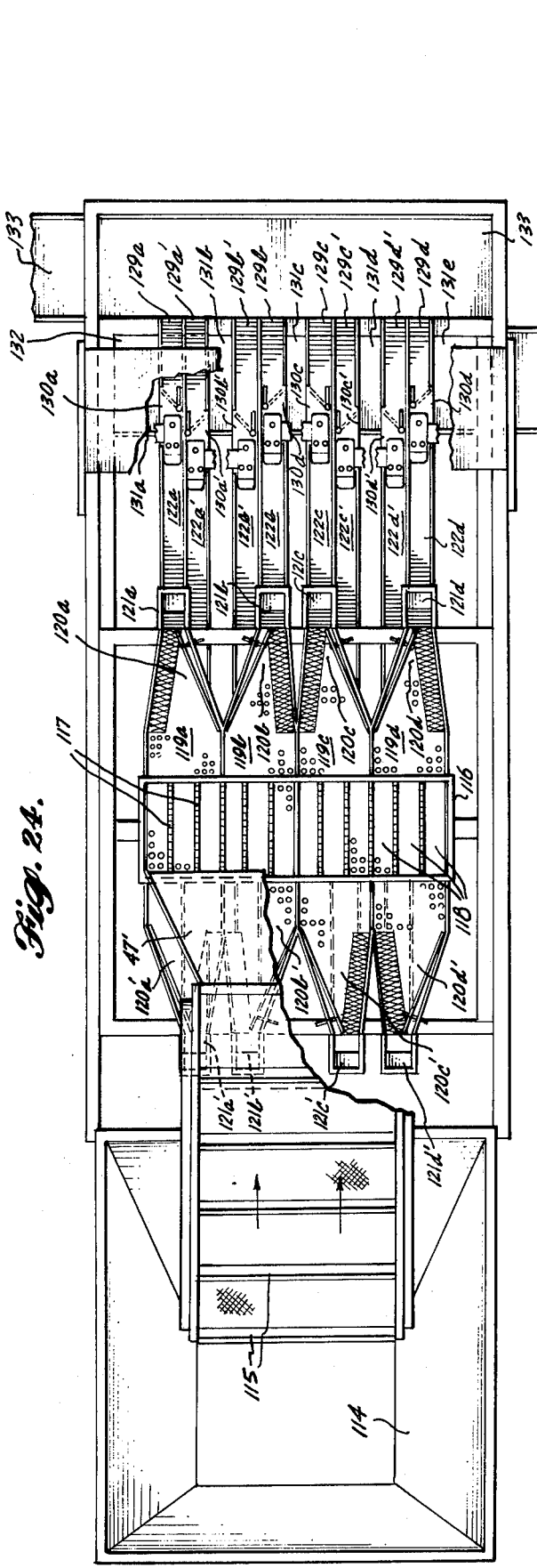
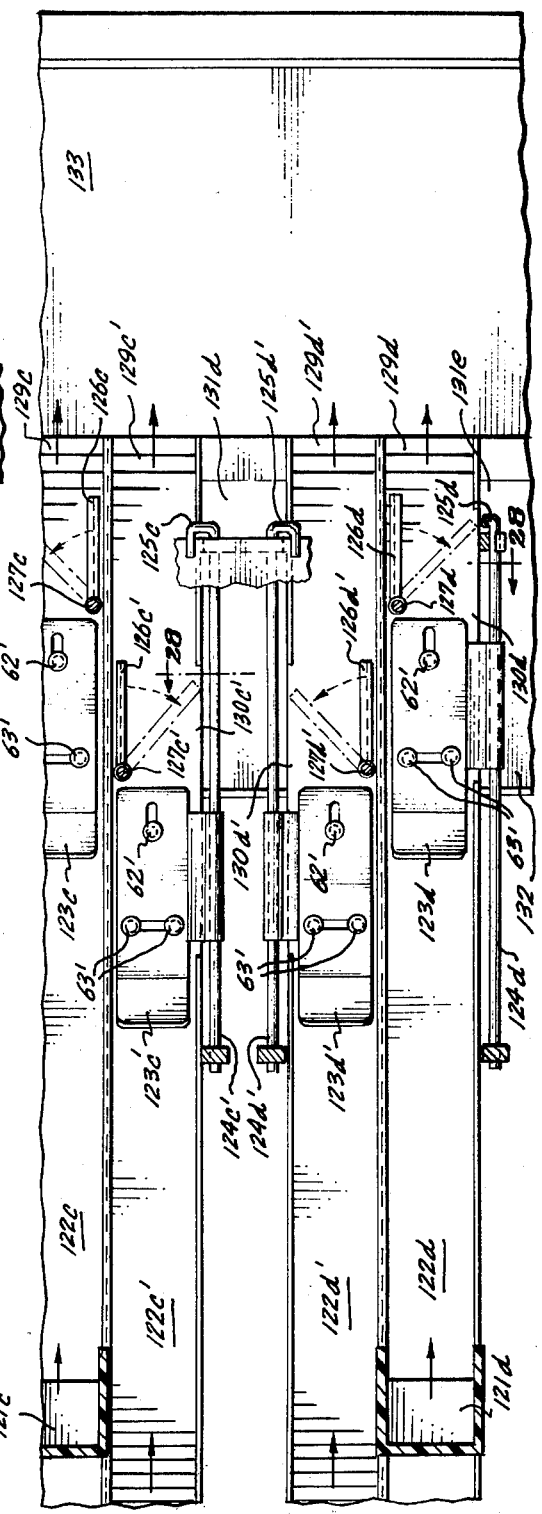

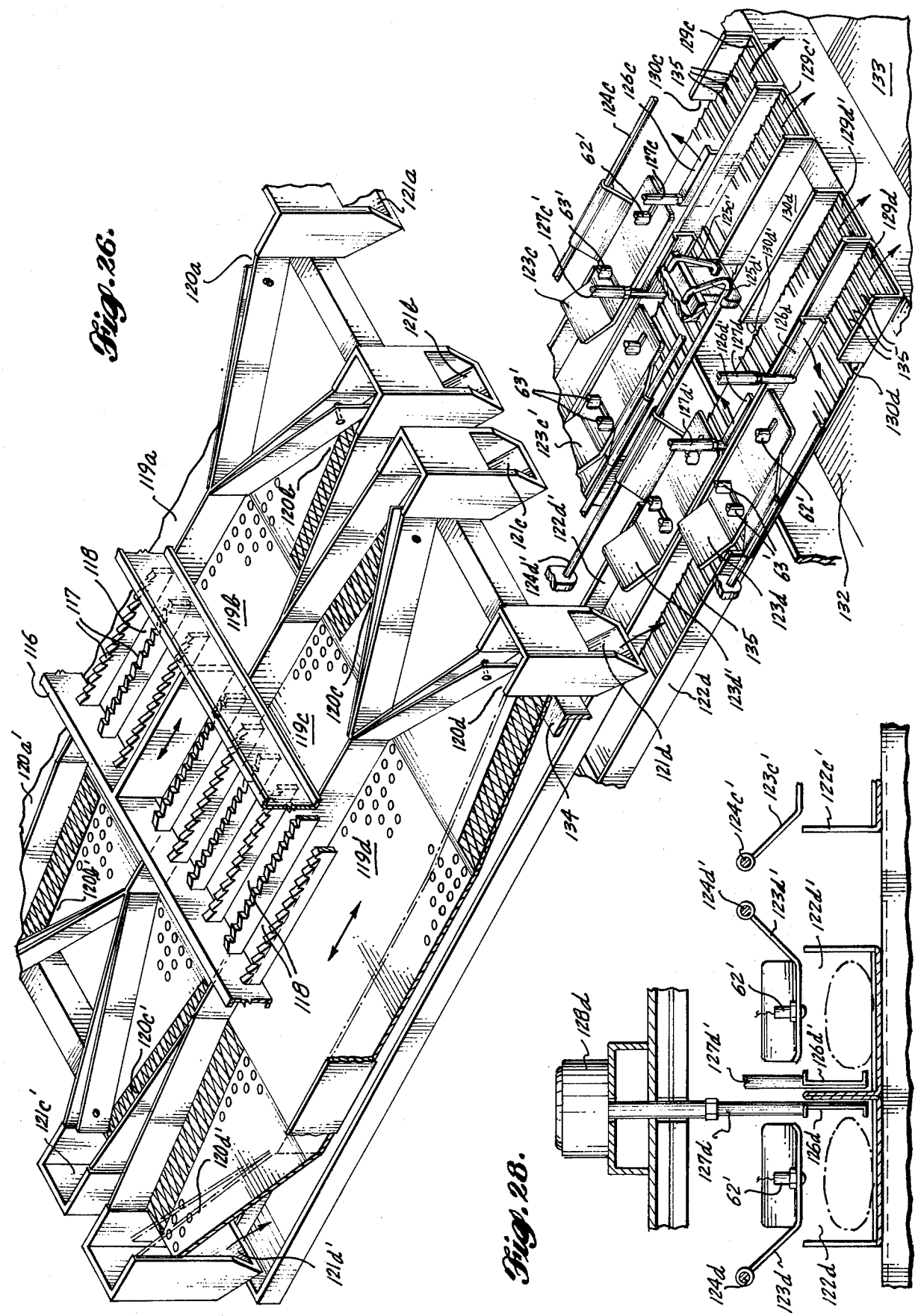

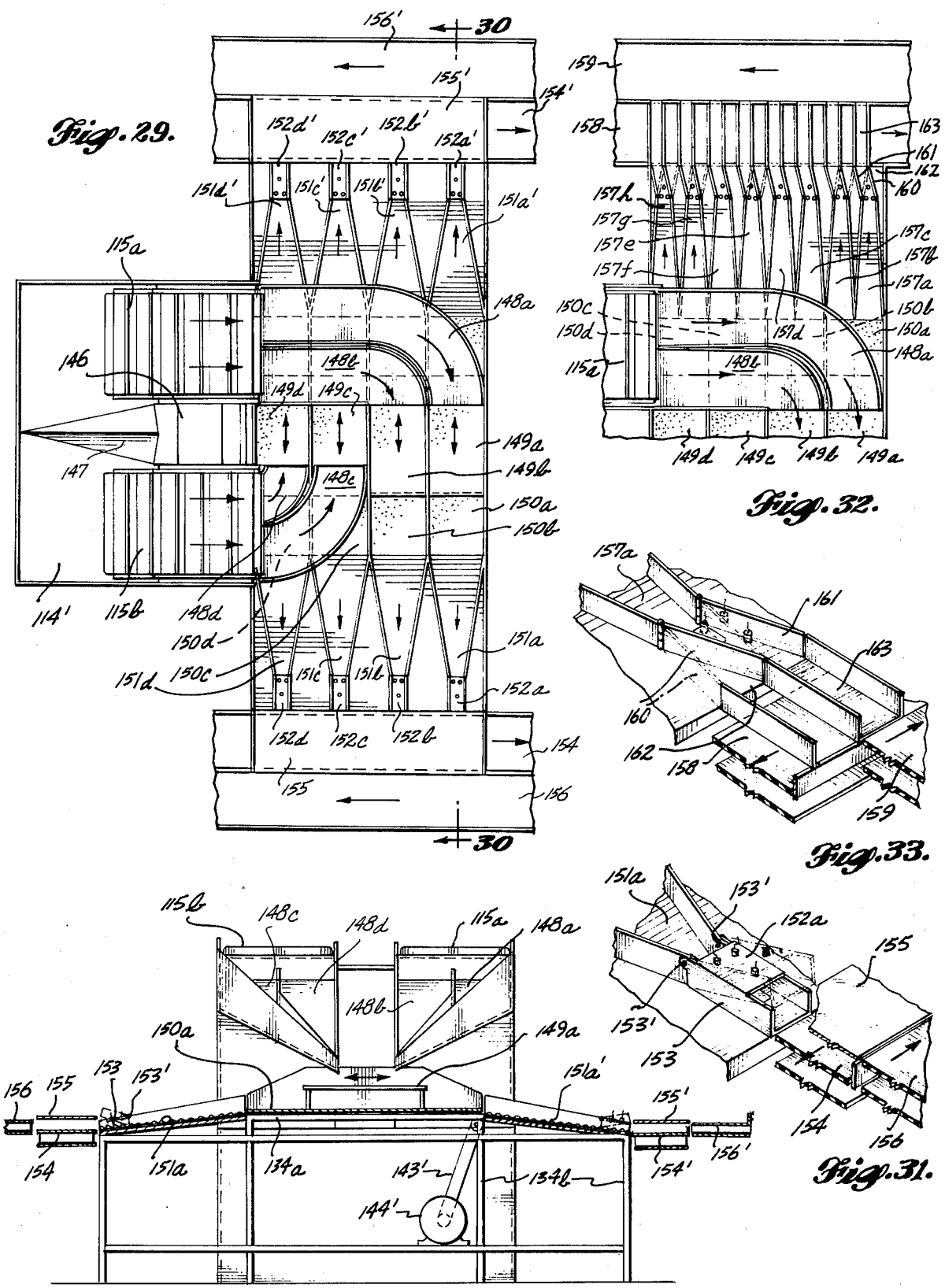

FISH CHARACTERISTIC DETECTING AND SORTING APPARATUS

This invention relates to mechanism for detecting a characteristic of fish and utilizing operation of such mechanism to actuate a signal or to effect a fish-sorting operation.

BACKGROUND OF THE INVENTION

1. Field of the Invention

Processing of fish for the recovery of fish eggs or for filleting has in the past required much handwork and has been wasteful of labor and fish. To harvest fish eggs all of the fish in a batch have been processed indiscriminately, although less than half of the fish have yielded any substantial quantity of eggs because male fish do not produce eggs, and eggs in some females may be too immature for the desired use.

In a fish-filleting operation, it may be uneconomical to fillet a fish of less than a predetermined size. Also, in order to accomplish the most effective fish-filleting operation, it is desirable for the fish to be oriented with its back at one predetermined side and its belly at the opposite side.

The present invention provides an apparatus and method for orienting and sorting fish automatically in accordance with particular characteristics to facilitate processing of the fish for a particular purpose.

If eggs are to be harvested from fish, the apparatus and method of the present invention can be utilized to sort the fish according to their sex. A female fish containing eggs is much more transparent than a male fish. Consequently, utilization is made of the transparency characteristic of such fish as a basis for simply determining their sex or actually to sort the fish into two classifications, male and female. As used in the following description "transparent" refers to the ability to transmit radiant energy whether or not such energy is visible light, and "opaque" refers to the substantial inability to transmit radiant energy.

Alternatively, for filleting purposes, for example, fish can be sorted into classifications, one class of which contains only fish of a sufficient size to be filleted effectively and oriented so that the back of each fish faces in a predetermined direction. The other class would include fish not of a proper size or not properly oriented for filleting.

2. Prior Art

Prior patents pertaining to the sorting of herring as to sex are Norwegian Pat. No. 90487, entitled Method for Sorting Herring and Fish and Apparatus for Carrying Out the Method, issued Nov. 25, 1957, and Cuthbert U.S. Pat. No. 3,859,522, for Method for Nondestructive Testing of Fish for Sex.

SUMMARY OF THE INVENTION

A principal object of the invention is to provide a detector which will detect a characteristic of fish and which will operate to indicate such characteristic or to sort fish in accordance with such characteristic.

In order to facilitate sorting of fish in response to a characteristic of the fish detected, it is an object to orient the fish for movement headfirst along a predetermined path in single file and spaced apart an appreciable distance.

Another object is to provide apparatus for detecting a characteristic of fish irrespective of ambient light conditions in which the operation is conducted.

It is also an object to effect a sorting operation quickly and with minimum manipulation of fish, even though the fish are fed to the sorting apparatus in indiscriminate attitude.

A further object is to be able to adjust fish-sorting apparatus of this invention to accomodate fish of considerably different average size and to be able to adjust the speed with which fish are sorted.

An additional object is to provide fish-sorting mechanism and mechanism for indicating a characteristic of a fish which is very reliable, while operating at high speed.

The foregoing objects can be accomplished by apparatus for sorting fish comprising detector means for detecting a characteristic of fish, fish-moving means for moving fish past the detector means, and channeling means operable in response to the detector means to channel fish in accordance with the effect of the fish on the detector means.

Also, in accomplishing the aforementioned objects, the method of sorting fish can be employed which comprises moving fish along a predetermined path, during movement of the fish along such path detecting a characteristic of the fish, and, after detecting the characteristic, moving the fish in a predetermined manner corresponding to the characteristic detected.

For sorting fish in accordance with the foregoing objects, the method may also comprise laying fish on a rough surface, vibrating such surface to move generally parallel to such surface, and during such vibration restricting movement of the fish along a path narrower than the length of the fish.

BRIEF DESCRIPTION OF THE DRAWINGS

FIG. 1 is a plan of apparatus for sorting fish and detecting a characteristic of fish, having parts broken away.

FIG. 2 is a vertical section through such apparatus taken along line 2—2 of FIG. 1 with parts broken away.

FIG. 3 is a plan of the right portion of the apparatus of FIG. 1 showing parts in different positions.

FIG. 4 is a vertical section through the apparatus taken on line 4—4 of FIG. 3.

FIG. 5 is a top perspective of the right portion of the apparatus shown in FIG. 1 with parts in exploded relationship.

FIG. 6 is a detail vertical section through a portion of the apparatus taken on line 6—6 of FIG. 1.

FIG. 7 is a top perspective of the apparatus shown in FIG. 1 with parts broken away.

FIG. 8 is a side elevation of the apparatus shown in FIG. 1 having parts broken away.

FIG. 9 is an enlarged detail elevation of the characteristic-detecting portion of the apparatus with parts broken away.

FIG. 10 is a transverse vertical section through the detecting portion of the apparatus taken on line 10—10 of FIG. 9.

FIG. 11 is an enlarged detail elevation of an alternative type of fish-feed mechanism that can be used in the apparatus.

FIG. 12 is an enlarged fragmentary elevation of another form of feed mechanism.

FIG. 14 is a top perspective of an alternative type of fish-orienting and singling mechanism.

FIG. 15 is a plan of such alternative type of orienting and singling mechanism.

FIG. 16 is a transverse section through such alternative type of fish-orienting and singling mechanism taken on line 16—16 of FIG. 15 and having parts broken away.

FIG. 17 is an enlarged detail perspective of a portion of a further modified fish-orienting and singling mechanism with parts broken away.

FIG. 18 is a top perspective of a further type of fish-characteristic detecting and channeling mechanism.

FIG. 19 is a transverse section through such further type of fish-characteristic detecting mechanism taken on line 19—19 of FIG. 18.

FIG. 20 is a horizontal section through such further type of fish-characteristic detecting mechanism taken along line 20—20 of FIG. 19.

FIG. 23 is a side elevation of a further form of fish-sorting apparatus.

FIG. 24 is a plan of such apparatus with parts broken away.

FIG. 25 is a fragmentary plan of a portion of such apparatus.

FIG. 26 is a top perspective of such apparatus with parts broken away.

FIG. 27 is a detail fragmentary side elevation of a portion of such apparatus with parts broken away taken on line 27—27 of FIG. 25.

FIG. 28 is a fragmentary vertical transverse section through a portion of the apparatus along line 28—28 of FIG. 27.

FIG. 29 is a plan of still another embodiment of the fish-sorting apparatus, and FIG. 30 is a vertical section through such apparatus taken on line 30—30 of FIG. 29.

FIG. 31 is a detail top perspective of a portion of the apparatus shown in FIGS. 29 and 30.

FIG. 32 is a fragmentary plan of still a further modification of the apparatus, and FIG. 33 is a detail top perspective of a fragmentary portion of this apparatus.

Figure 13:
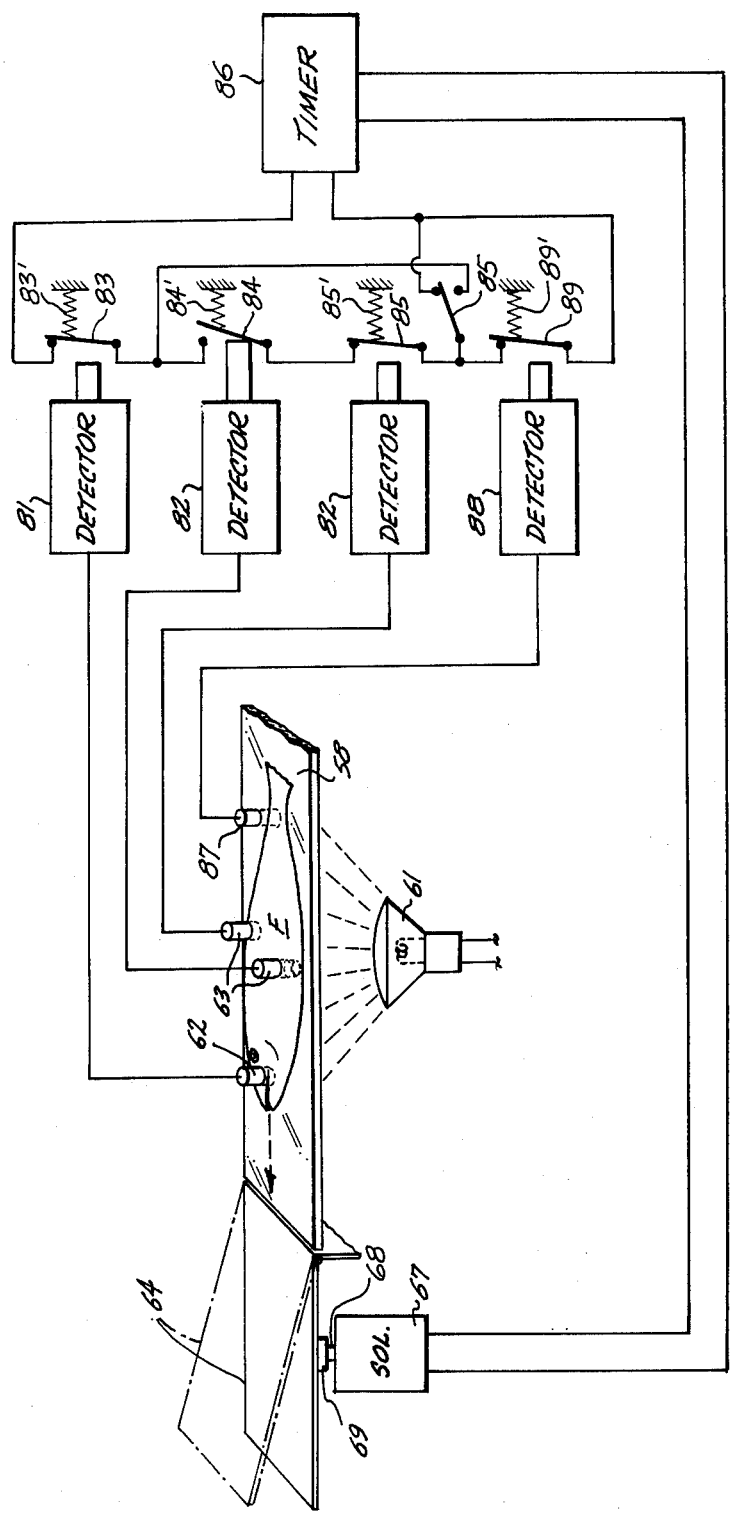
FIG. 13 is a diagrammatic electric circuit diagram of fish-characteristic detector mechanism.

In sorting fish for harvesting eggs or in preparing for a filleting operation, the first step is to orient the fish for enabling them to be tested and sorted effectively. The most desirable orientation for the fish is to move them along a path in spaced single-file procession oriented headfirst. Fish can be thus oriented and tested by the apparatus shown in FIGS. 1 to 10 inclusive. The fish are oriented headfirst and singled by the action of the apparatus designated 1 in FIG. 1. The fish are accelerated in the section designated 2 to space them apart appreciably, and a characteristic of the fish, such as their relative transparency, is detected in section 3 to indicate whether the fish are females or males.

By use of the orienting apparatus shown in FIGS. 1 to 8 inclusive, the fish can be oriented headfirst in single file even though they are initially fed to the apparatus in variable quantities and in random orientation or disarray. The fish are deposited in disarray on a rough surface 4 forming the bottom of a trough between a concave wall 5 and a convex wall 6 which is of larger radius than wall 5 to form a crescent-shaped trough. The width of the trough can be varied by adjusting sliding clamps 7 along radial slots 8 to alter the spacing between the opposite walls of the trough at different locations along its arcuate length. By such adjustment, the widths of the discharge opening 9 at each end of the orienting trough can be adjusted. The width of each discharge opening should be slightly greater than the maximum width of the largest fish to be processed in a given batch, but much smaller than the length of the smallest fish. Furthermore, the width of the trough over the major portion of its length at each side of its center will be less than the length of the shortest fish to be oriented.

Whatever the adjustment of the sliding clamps 7 along their slots 8 may be, the trough should taper from its central portion toward its ends so that such trough is of truncated-cresent shape in order for the discharge openings to supply parallel fish-sorting lines. Fish dumped in the central portion of such crescent trough will migrate toward the opposite ends of the trough headfirst if the trough is vibrated lengthwise of the trough, such as being oscillated. If the fish have been scaled, the sides of the fish are unidirectionally rough so that movement of the trough bottom toward the tail of a fish will cause the surface 4 to slide relative to the fish, whereas movement of the trough bottom toward the head of the fish will propel the fish headwise. Each fish in the trough, therefore, migrates by incremental steps to th discharge end 9 toward which the fish head is directed. Fish thus oriented pass through the discharge openings 9 of the trough ends across bridge troughs 10 to the accelerating section 2 of the apparatus.

As mentioned above, fish progress from the central portion of the orienting trough toward its ends by vibration of the bottom 4 of the trough. Such trough bottom is formed by table 11 which is supported from a base 12 in generally horizontal position, although it may be inclined slightly from the central portion of the trough toward the discharge openings 9. One side of the table 11 can be connected to the frame 12 by a clevis 13 fitting over the swingable free end of a cantilever spring plate 14. The root of such spring plate is bolted or otherwise secured to a rigid post 15. As shown in FIG. 5, a shock-absorbing connection is effected between the clevis 13 and the end of spring plate 14 by fitting elastomer blocks 16 within the clevis on opposite sides of the spring plate end and holding the assembly together by a bolt 17 extending through apertures in the clevis 13, elastomer blocks 16 and the end of spring plate 14 and secured by a nut 17'.

The table 11 has another connection to the post 15 at a location approximately 90° from the clevis 13. A second clevis 18 fits over the swingable free end of a second spring plate 19 having its root end anchored to the fixed post 15. Spring plate 19 extends approximately perpendicularly to the spring plate 14, as shown in FIGS. 3 and 5. The clevis 18 is spaced from the free end of spring plate 19 by elastomer blocks 20 at opposite sides of the spring plate. The clevis, the free end of the spring and such blocks are secured together by a bolt 21 extending through apertures in such clevis, spring end and blocks and secured by a nut 21'.

The table 11 is approximately semicircular in shape, and the quadrant 22 is secured to the swinging ends of spring plates 14 and 19, as described above. The other quadrant 23 of the table rests on an arcuate facing 24 of Teflon or other slippery material on the upper side of an arcuate band 25 of approximately quadrant shape supported from the base 12 independently of spring plates 14 and 19. One end of the arcuate band 25 has a clevis 26 fitting over the swinging free end of a spring plate 27, the root portion of which is anchored to post 15. Elastomer block 28 is interposed between the opposite sides of the free end of spring 27 and clevis 26. A bolt 29, extending through apertures in the clevis, the elastomer blocks 28 and the free end of spring plate 27 is secured by a nut 29' to hold these parts together. The clevis 30, carried by the opposite end of the arcuate band 25, fits over the swingable free end of spring plate 31, the root portion of which is rigidly anchored to the post 15. As shown in FIGS. 2 and 4, elastomer blocks 32 are located between the opposite sides of the free end of spring plate 31 and the clevis 30. The clevis, spring plate end and blocks 32 are secured together by a bolt 33 extending through apertures in the clevis, the spring plate end and the blocks 32 and secured by a nut 33'.

The pair of spring plates 14 and 19 and the pair of spring plates 27 and 31 are moved relative to each other in an oscillating fashion by the free ends of spring plates 19 and 31 first being forced apart and then freed so that such spring plates can swing toward each other. Such movement is effected by forcing apart abutment rollers 34 shown in FIGS. 2 and 4 mounted on stems 35 which are apertured to be secured by bolts 21 and 33, respectively, to clevis 18 mounted on the table and clevis 32 mounted on the arcuate supporting strip 25.

Inorder to balance the vibrating forces, the weight supported by spring plates 14 and 19 should be approximately equal to the weight supported by the spring plates 27 and 31. Because the structure of the arcuate strip 25 is so much smaller than the structure of the trough table 11, an arm 36 is attached to the arcuate band 25 and projects generally radially inward from it. A weight 37 is carried by the arm 36 and, preferably, can be adjusted to different positions along the length of the arm.

While general reference is made to vibrating the table 11, best results are accomplished by moving the table in a particular fashion. As has been mentioned, it is desirable that the table move principally lengthwise of the trough so that fish lying on the trough bottom 4 are moved in the directions indicated by the arrows on the fish in FIG. 3. The purpose of such table movement is to effect intermittent movement of the table toward the head of the fish to propel it toward a discharge opening 9 at one end of the trough. Since the trough is arcuate, it is preferred that the table 11 oscillate substantially around post 15 as its center. Further, it is desirable to minimize unbalanced vibrations of the apparatus which would tend to cause the apparatus to be bodily displaced. Substantial balancing of the forces on the apparatus is accomplished by making the table 11 and the components associated with the supporting band 25 of approximately equal weight and to move the two main components of the vibrating system through approximately equal amplitudes in opposite directions.

By the structure described above, the table 11 and the arcuate band assembly 25 can be made of approximately equal weight. These components can be oscillated with approximately equal amplitude by wedging rotary inclined thrust plates 38 and 39 against abutment rollers 34. Such thrust plates are mounted on axle 40 which is journaled in posts 41 and base 12. The thrust plates 38 and 39 are held in equally oppositely inclined attitudes by a tapered spacer block 42 mounted between them. The axle 40 is rotated by a belt and pulley drive 43 driven by a countershaft 44 which in turn is rotated by the drive belt 45 driven by motor 46, as shown in FIG. 8.

As the axle 40 turns the thrust plates 38 and 39 to the position of FIG. 4, the abutment rollers 34 are forced apart to their fullest extent which moves the swinging ends of spring plates 19 and 31 apart to the positions shown in broken-lines in FIG. 3. In such positions, the spring plates 14, 19, 27 and 31 are stressed so that when the thrust plates have rotated through an angle of 180° to the positions of FIG. 2, the resilience of the spring plates will swing the abutment rollers toward each other to retain them in contact with the thrust plates 38 and 39. As the shaft 49 continues to rotate, the thrust plates will again wedge the abutment rollers 34 apart to the positions of FIG. 4. Continued rotation of shaft 40 will cause the abutment rollers alternately to be wedged apart by the thrust plates 38 and 39 and to be returned toward each other by the resilience of the spring plates 14, 19, 27 and 31. Consequently, the table 11 will execute repeated oscillations while its quadrant 23 slides on the Teflon facing 24 of arcuate table-supporting band 25.

Even though, when initially deposited from feed trough 47 into the central portion of the orienting trough, the fish in some instances may lie in stacked relationship as shown in FIG. 6, the movement of the rough trough bottom 4 relative to a fish lying on it will cause such fish to move in the direction indicated by the arrow in FIG. 6 so as to slide such a fish out from under an upper fish which will not be moved lengthwise because it is held out of contact with the rough surface 4. As a fish is slid out from under the upper fish, such upper fish will come into contact with the rough surface 4, whereupon it also will be shifted progressively lengthwise toward a discharge opening 9.

Fish expelled out of the discharge openings 9 by the oscillating trough will slide across the connecting troughs 10 into the accelerating section of the apparatus. FIGS. 1, 7 and 8 show such accelerating sections as including a transport belt 48 carried by pulleys 49 and 50 and supported by a backing plate 51. Such belt is tightened by a belt-tightener 52 engaging the lower stretch of the belt. The pulley 50 is mounted on axle 53 carrying pulley 54 which is driven by belt 55 from countershaft 44. The ratio of the pulleys carrying belt 55 can be selected so as to propel belt 48 at a speed appreciably greater than the speed at which fish are discharged through the openings 9 by the oscillating rough trough bottom 4.

As each fish is discharged through opening 9 and across bridge trough 10, it will be accelerated by being carried on belt 48, so as to have been moved a substantial distance from the discharge end of trough 10 before the next fish is discharged onto the belt. Since the width of the discharge openings 9 is only slightly greater than that of the widest fish, the fish will be discharged in single file through the discharge openings. Therefore, sections 1 and 2 cooperate to form a singling device. The acceleration of fish by the belt 48 will cause the fish to enter the discharge trough 56 of the accelerating section in single file and in appreciably spaced relationship.

From the accelerating section, each fish enters the tubular passage 57 to the characteristic-detecting section 3. While, as shown best in FIG. 10, the cross section of the tube 57 may be circular, it is preferred that the cross section of the tube forming the path of the fish past the characteristic-detector mechanism be substantially semicircular. Such section may have a semicylindrical floor portion 58, as shown in FIGS. 9 and 10, and a flat, diametral, planar cover 59. The bottom section 58 has windows 60 in it along its length through which radiant energy, such as infrared rays, can be projected from a suitable source 61 of radiant energy, shown in FIG. 1 and FIG. 7. Radiant energy projected through the windows 60 is received and detected by energy-responsive elements 62 and 63 mounted in the flat side 59 of the detector section.

The energy-responsive element 62 is spaced further along the path of movement of the fish through the tube 57, 58, 59 than the energy-responsive elements 63. Passage of the head beneath element 62 conditions the detecting circuit described below to respond to energy received by elements 63. The spacing between elements 62 and 63 is sufficient to insure that the characteristic of the fish to be detected, such as the transparency of the fish, will be tested at the time that the head of the fish is interposed between the energy-responsive element 62 and its energizing source. The energy-responsive elements 63 are spaced apart transversely of the path of fish movement, as shown best in FIG. 10.

Beyond the fish-characteristic detecting section of the apparatus is located channeling means actuated by the energy-responsive means. Such channeling means is shown in FIGS. 7 and 8 as including a transfer trough section 64 having its end remote from the characteristic-detecting section of the apparatus movable between positions in alignment with two discharge troughs 65 and 66. A solenoid 67 having a plunger 68 attached at 69 to the bottom of the channeling transfer trough section 64 selects the upper discharge trough by shifting the channeling trough. Energization of the solenoid 67 will indicate the characteristic detected by shifting plunger 68 upward to align the discharge end of trough 64 with the upper trough 66. When solenoid 67 is deenergized, a tension spring 70 will return the channeling trough section 64 downward so that its discharge end again is aligned with the lower trough 65.

Fish delivered at random through feed trough 47 to the central portion of the orienting trough 4, 5, 6 lie to a greater or lesser extent on the rough bottom 4 of such trough. As the trough is oscillated, the fish will be moved progressively headfirst toward the discharge openings 10 at the opposite ends of the trough. The fish will move through such discharge openings and the bridge troughs 10 and will be accelerated by being carried by the belts 40 so as both to move successive fish apart an appreciable distance and to impart sufficient momentum to the fish to slide them successively through the tube 57, the characteristic-detecting trough 58, the channeling trough 63 and one of the discharge troughs 65, 66.

Instead of utilizing belts 48 to accelerate the fish sufficiently so that their momentum will carry them through the fish-characteristic detecting section of the machine, vibrating pusher means can be used, such as the toothed conveyor shown in FIG. 11. A lower plate 71 having pusher teeth to exert a greater push on the fish when the plate is moving in one direction than when moving in the opposite direction is mounted on movable ends of spring leaves 72. Such plate is vibrated or reciprocated longitudinally of the fish. An upper, similarly toothed hold-down plate 73 can bear on the upper side of the fish, which plate may be stationary or may be reciprocated opposite to the phase of lower plate 71. The teeth 74 of the lower plate and the teeth 75 of the upper plate are inclined in the direction of the desired movement of the fish. Such teeth may have a pitch of approximately one inch. Hold-down springs 76 confined in cups 77 and reacting from backing members 78 press downward on the upper side of upper plate 73 to hold the fish against the teeth 74 of the lower plate 71. As the plate 71 is reciprocated to the right, engagement of the teeth 75 of upper plate 73 with the fish will deter retrograde movement of the fish. When the movement of plate 71 again is reversed so that it moves to the left, the teeth 74 will engage the sides of the fish and effect a further incremental movement of the fish to the left. The stroke of the plate or plates may be about 2 inches and the frequency of reciprocation several cycles per second.

Another alternative for accelerating the fish in section 2 of the apparatus, in lieu of belts 48, is the arrangement of brushes shown in FIG. 12. Any number of rotary brushes can be employed. Lower brushes 79 are shown in FIG. 12 as being mounted immediately at the discharge end of bridge trough 10 in lieu of a belt 48. The fish is pressed against the brushes 79 by upper brushes 80 which are either resiliently mounted or which are mounted sufficiently close to lower brushes 79 so that both sides of a fish received between the brushes will always be engaged by the bristles of both the upper and lower brushes. The rotary brushes 79 and 80 are then rotated in a direction to shift fish F to the left as seen in FIG. 12.

A representative circuit diagram of the apparatus is shown in FIG. 13 as including a detector 81 for the energy-responsive element 62 and detectors 82 for the energy-responsive elements 63. The detector 81 controls a switch 83 and the detectors 82 control switches 84. A switch 85 in its upper position of FIG. 13 enables a circuit to be completed to a timer 86, when all of switches 83 and 84 are closed.

The switches 83 and 84 are normally closed by compression springs 83' and 84' so that, when the energy-responsive elements 62 or 63 are energized by energy from the energy source 61, the corresponding switches will be opened. As long as there is no fish in the trough 58, therefore, the elements 62 and 63 will be energized and the switches 83 and 84 will be held open. Consequently, solenoid 67 is normally in deenergized condition and swinging transfer trough section 64 is in the solid-line position of FIG. 13. When the head of the fish F obscures the energy-responsive element 62 from the source of energy 61, tge detector 81 will be deenergized to permit switch 83 to close and thereby condition the circuit to respond to signals from elements 63. If the fish belly is sufficiently transparent so that one of the energy-responsive elements 63 is energized by the energy source 61, the switch 84 of the corresponding detector 82 will be opened so that a circuit cannot be completed to the timer 86 through the switch 85. Consequently, the solenoid 67 will remain deenergized and the fish will slide along the troughs 58 and 64 into the lower trough 65. Such fish will be a female.

A male fish F is sufficiently opaque so that insufficient energy is received by element 62 and by both elements 63 to effect energization of the detectors 81 and 82, and all of the switches will be closed by their springs to complete the circuit through switch 85 to the timer. Consequently, a predetermined period of time after the energy-responsive elements 62 and 63 have all been obscured, the timer 86 will energize solenoid 67 to project plunger 68 for swinging transfer trough section 64 to channel the male fish into upper discharge trough 66.

The same general type of circuit can be used to determine the length characteristic of a fish. For such use an energy-responsive element 87 is located rearwardly of the elements 63. The energy-responsive element is connected to a detector 88 which controls a switch 89. To sort fish according to length, switch 85 will be moved to its lower position so as to connect a circuit bypassing the switches 84 of the detectors 82 for energy-responsive elements 63. Detectors 82 can, therefore, have no control over the energization of timer 86 whether or not the energy-responsive elements 63 receive energy from the energy source 61.

In a length-sorting operation, when the head of a fish obscures the energy-responsive element 62, detector 81 will permit closing of switch 83 by spring 83'. If the fish is not long enough so that its tail portion obscures energy-responsive element 87, the detector 88 will open switch 89 in opposition to spring 89' and the timer 86 and solenoid 67 will remain deenergized so that the detector trough 64 will remain in the solid-line position of FIG. 13 and the short fish will slide into discharge trough 65. If the fish F is sufficiently long to obscure energy-responsive element 87 simultaneously with energy-responsive element 62 being obscured by the fish head, as shown in FIG. 13, detector 88 will permit switch 89 to close so that the timer 86 will be energized through closed switches 83, 85 and 89. Such energization of the timer will effect delayed energization of solenoid 67 so that plunger 69 will raise trough 64 into the dot-dash position of FIG. 13. In such position, the fish having sufficient length will slide up the defector trough 64 into the upper discharge trough 64 so as to be segregated from the shorter fish.

An alternative type of orienting trough is shown in FIGS. 14, 15 and 16. In this construction, the table 11 is directly connected to springs 14 and 19, as described previously, and oscillates relative to the supporting band 25 carried by springs 27 and 31. In this instance, however, a compound type of trough is utilized. The end portion of such trough is composed of the rough bottom 4', the outer wall 5', and the inner wall 6'. The central portion of the compound trough is formed by the highest component of the trough including a rough bottom 90, a concave outer wall 91, and a convex inner wall 92. An intermediate trough section of greater arcuate extent than the upper trough section includes a rough bottom 93, an outer concave wall 94, and an inner concave wall 95.

Fish deposited into the upper trough section from chute 47 migrate from opposite ends of the upper trough component to the intermeidate trough component into which they drop. The fish can migrate in either direction headfirst in the intermediate trough section 93, 94, 95 to the lowest trough compoment 4', 5', 6' but cannot work their way up again into the central trough section 90. From the lowest trough component the fish cannot return to the intermediate trough section. Such a composite trough arrangement provides passages between adjacent trough section floors and thereby facilitates progression of fish headfirst when they must move over an arcuate extent exceeding 90° because the fish can pass beneath the newly supplied fish coming from chute 47.

In FIG. 17 the composite trough is similar to that described in connection with FIGS. 14, 15 and 16, except that fish which have migrated to the lower trough 4', 5', 6' and otherwise would be required to travel more than 90° in order to reach a discharge opening 9 can be discharged through the central outlet 96, carried away by belt 97 and returned through the feed chute 47 for reprocessing.

In FIG. 18 apparatus is illustrated for detecting color characteristics of fish which will indicate orientation of the back and belly of fish. As shown in FIG. 20, the back of many fish is darker than the belly. The object achieved by the use of this apparatus is to energize the solenoid 67 appropriately for reciprocating the armature 68 connected at 69 to the deflecting trough 64 so as to shift such trough from alignment with one discharge chute 65' to alignment with another discharge chute 66' depending on the back and belly orientation of the fish F.

The path defined by the detector trough 58' and the planar cover 59' is similar to that shown in FIGS. 1, 7, 8, 9 and 10 except that in this instance the arcuate extent of the trough wall 58' is greater than 180°, being, for example, somewhat over 200°. A source of radiant energy 98 is mounted in the upper wall 59', and energy-responsive elements 99 are located in opposite sides of the lower wall 58'. Radiant energy produced by the source 98 is directed onto the upper side of the fish F shown in FIG. 19 and will be reflected from the fish to the energy-responsive elements 99. More energy will be reflected from the light colored belly than from the dark back so that more energy will be received by the energy-responsive element 99 on the belly side of the fish path than by the energy-responsive means on the back side of the fish path.

The energy-responsive elements 99 will be connected in a suitable electric circuit with the solenoid 67, such as illustrated by the circuit diagram in FIG. 13, so that, when the energy-responsive element 99 at the left of FIG. 19 receives more radiant energy than the energy-responsive element 99 at the right of FIG. 19, the solenoid 67 will remain unenergized. Fish travelling through the transfer trough section 58' will, therefore, slide through the trough 64 in its lower position into the discharge trough 65'. When the fish is disposed with its back at the left and its belly at the right of FIG. 19, however, the energy-responsive element 99 at the right of that figure will receive more energy reflected from the fish belly than the left element 99 receives reflected from the fish back. Under those circumstances, the solenoid 67 will be energized to shift deflector trough 64 upward into the dot-dash line position shown in FIG. 18, so as to channel the fish sliding through trough 58' and deflector trough 64 upward into the discharge trough 66'.

Figure 21:
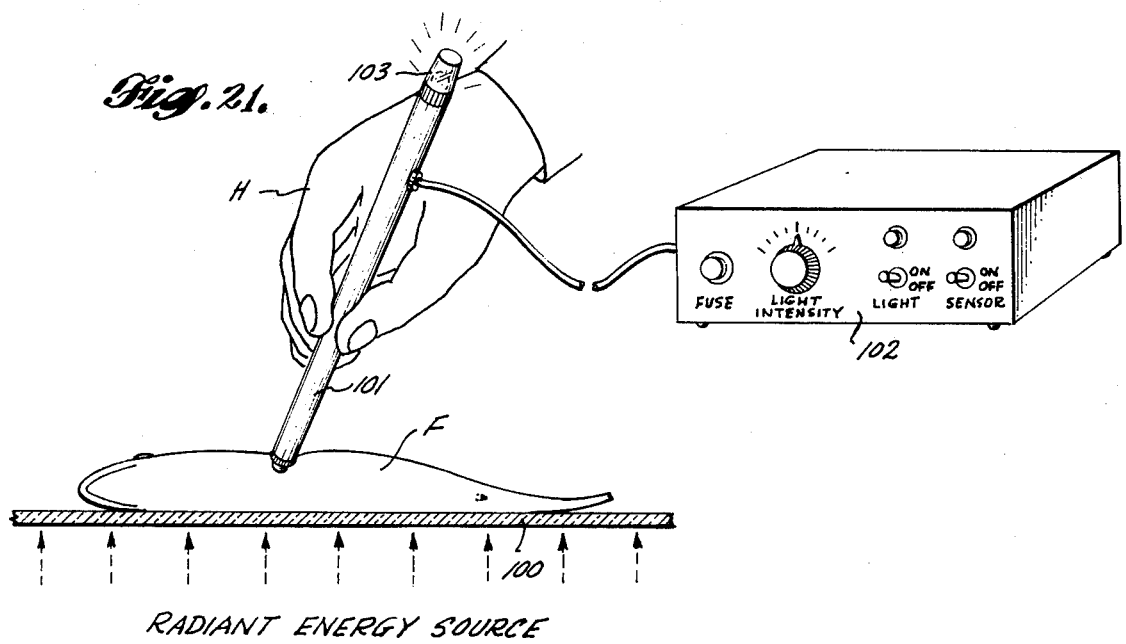
FIG. 21 is a view partly in vertical section and partly in perspective of fish-characteristic detector and signaling mechanism.

The type of apparatus shown in FIG. 21 simply indicates a characteristic of fish instead of activating mechanism to channel the fish to one discharge trough or the other in response to a characteristic detected, and may be portable. A transparent plate 100 is provided on which a fish F can be laid and through which radiant energy, such as infrared radiation or light, is projected upward. An energy-responsive element or sensor 101 held manually by the hand H can be applied to the upper side of the fish, and the amount of radiant energy that it receives will depend upon the degree of transparency of the fish. The intensity of the radiant energy generated by the source can be regulated by a suitable control of a control box 102. The energy-responsive element 101 is connected to such control box containing a circuit suitable for effecting energization of a signal light 103 when the radiant energy received by the energy-responsive element 101 exceeds a predetermined quantity. The amount of energy received will be dependent upon the transparency of the fish, and the transparency characteristic of the fish will be dependent upon whether the fish is a female or a male.

Figure 22:
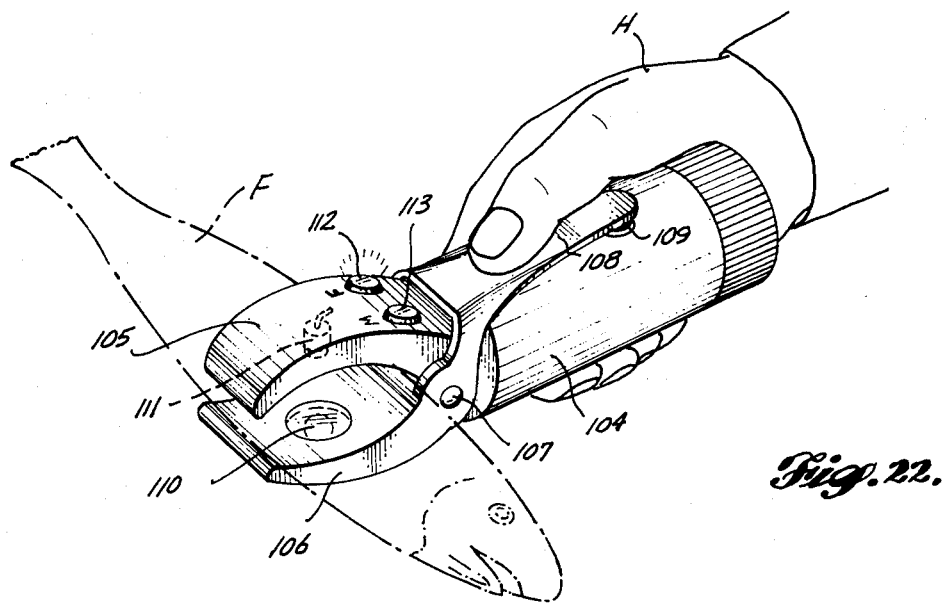
FIG. 22 is a top perspective of still a different type of fish-characteristic detector and signaling mechanism.

In FIG. 22 an alternate type of transparency indicator is illustrated which is portable and manually operated. In this instance, power for producing radiant energy is supplied by a battery in the case 104. The upper jaw 105 of a fish gripper is integral with the case 104. A movable jaw 106 cooperating with the fixed jaw 105 is connected to such fixed jaw by a pivot 107. A handle 108 is integral with the movable jaw 106, and the swingable end of such handle is located to depress a switch button 109 when the swingable handle is pressed toward the case 104.

A radiant-energy source 110 is mounted in the movable jaw 106 and suitably connected in circuit with a battery in case 104 and switch 109. The upper fixed jaw carries an energy-responsive element 111 and indicator lights 112 and 113. The energy-responsive element 111 is connected in circuit with the indicator lights 112 and 113 so that if an amount of radiant energy exceeding a predetermined quantity is received by the energy-responsive means 111 when the handle 108 is depressed to close the switch 109, the light 112 will be illuminated to indicate that the fish is a female. On the other hand, if the fish is sufficiently opaque so that the amount of radiant energy received by the energy-responsive element 111 from the radiant-energy source 110 when the jaws 105 and 106 grip a fish is less than a predetermined amount, the light 113 will be energized indicating that the fish is a male.

FIGS. 23 to 28, inclusive, show another form of apparatus for mechanically sorting fish such as herring according to their sex in a fully automatic operation. Fish of both sex are dumped at random into the hopper 114. From such hopper, the fish are lifted and drained by the endless elevator conveyor 115 to the feed chute 47'. From such feed chute the fish drop into the distribution and preliminary orientation trough 116. Such trough has an open bottom and parallel bars 117 extend across its width. The upper edges of such bars are sawtoothed with the teeth of alternate bars raked in the same direction, and the teeth of adjacent bars raked in opposite directions. The width of the trough exceeds the length of the longest fish to be processed, and the spaces 118 between the bars are wider than the width of the largest fish to be processed but are not appreciably wider than the width of a single large fish, so that fish having their lengths extending transversely of the trough can drop through the spaces 118 between the bars 117 with their lengths generally parallel.

Beneath the distribution and preliminary orientation trough 116 are passageways 119a, 119b, 119c and 119d arranged with their lengths parallel and extending transversely of the length of the trough 116. At one side of such trough the ends 120a, 120b, 120c and 120d of such passageways converge to discharge chutes 121a, 121b, 121c and 121d, respectively. At the opposite side of the trough 116 the end portions 120a', 120b', 120c' and 120d' of the passageways 119a, 119b, 119c and 119d, respectively, converge to discharge chutes 121a', 121b', 121c' and 121d', respectively.

Beneath the discharge chutes 121a, 121b, 121c and 121d, respectively, are sorting troughs 122a, 122b, 122c and 122d. Correspondingly, beneath the discharge chutes 121a', 121b', 121c', and 121d', respectively, are sorting troughs 122a', 122b', 122c' and 122d'. The relationship between the discharge chutes and the parallel sorting troughs is shown generally in FIG. 24, and is shown more specifically for representative troughs 122c, 122c', 122d' and 122d in FIG. 25.

Each of the sorting troughs includes a fish sex-detecting station shown generally in FIGS. 25 and 26 and in greater detail in FIGS. 27 and 28. At each sex-detecting station the bottom portion of each sorting trough includes one or more transparent sections 60 through which radiant energy can be projected upward into the trough from a radiant-energy source 61 located beneath the trough. Radiant-energy responsive devices 62' and 63', such as photoelectric cells, are carried by mounting plates 123a, 123a', 123b, 123b', 123c, 123c', 123d and 123d' corresponding to the several sorting troughs. Such mounting plates are swingably supported in cantilever fashion on rods 124a, 124a', 124b, 124b', 124c, 124c', 124d and 124d', respectively, which extend alongside and above the respective sorting troughs, as shown in FIGS. 25, 26 and 28.

Ends of the rods carrying the mounting plates for the radiant-energy responsive devices are bent to form handles represented by handles 125c', 125d' and 125d shown in FIGS. 25, 26 and 27 at locations where they can be grasped by an operator and swung to swing, respectively, the mounting plates 123c, 123c', 123d' and 123d to retract them upward from their generally horizontal positions parallel to the bottoms of the sorting troughs, as shown in FIG. 28. Normally, the bent handles of the rods engage a plate, as shown in FIGS. 25 and 26, to limit the downwardly swung positions of the mounting plates. From such positions the plates can be swung upward through angles of approximately 90° to afford access to the sorting troughs for cleaning or to release a jam of fish which may have accumulated in a sorting trough.

Passage along the sorting troughs to their ends is controlled by gates 126a, 126a', 126b, 126b', 126c, 126c', 126d and 126d', respectively. The gates are supported for swinging between positions parallel to and alongside the trough edges and inclined positions extending across the respective troughs by upright suspension rods including rods 127c, 127c', 127d' and 127d shown in FIGS. 25 and 26, as representative. Each of these rods is turned about a vertical axis by a rotary drive actuator such as torsional solenoids 128d' and 128d shown in FIGS. 27 and 28, respectively, as representative.

When any gate 126a to 126d' is in a position parallel to and alongside a side of one of the sorting channels 129a, 129a', 129b', 129b, 129c, 129c', 129d or 129d', as shown in FIG. 24, fish moving along such channel will be discharged lengthwise from the end of the channel. Any diverting gate which is swung to its inclined position illustrated for gates 126c, 126c', 126d' and 126d as dot-dash lines in FIG. 25, on the other hand, will shunt the fish through a side opening, such as 130c, 130c', 130d' or 130d, as shown in FIG. 25. Fish shunted through such a side openings will fall through one of the upright passages 131a, 131b, 131c, 131d or 131e onto a conveyor 132. It will be seen best from FIG. 24 that the sorting troughs 122a to 122d' are arranged in pairs including paired troughs 122a and 122a', paired troughs 122b and 122b', paired troughs 122c and 122c' and paired troughs 122d and 122d'. These trough pairs are spaced apart to provide shared upright passages between spaced pairs of troughs. Upright passage 131a receives fish only from opening 130a of trough 122a and upright passage 131e receives fish only from opening 130d in trough 122d. Passage 131b, however, receives fish both from opening 130a' of trough 122a' and from opening 130b' of trough 122b'. Similarly, upright passage 130c receives fish both from opening 130b of trough 122b and from opening 130c of trough 122c. In addition, upright passage 131d receives fish both from opening 130c' of trough 122c' and from opening 130d' of trough 122d'.

Fish falling through upright passages 131a to 131e are deposited on a discharge conveyor 132, whereas fish discharged from the ends of the sorting troughs 129a to 129d', inclusive, fall onto a discharge conveyor 133.

In order to propel fish reliably and quickly through the sorting apparatus, the same general type of feeding mechanism as disclosed in FIGS. 1, 3, 5 and 6 can be used. Any fish deposited on the bars 117 can be swung into general alignment with such bars to fall between them by reciprocating the distribution and orientation trough 116 in a direction lengthwise of the bars. The teeth raked in one direction will tend to move the portion of a fish engaging them in the direction of rake, whereas another portion of the fish engaging teeth raked in the opposite direction on the adjacent bar will tend to move the latter portion of the fish in the direction opposite that in which the first portion of the fish is moved. By thus exerting a force couple on the fish, it will be swung until its length is sufficiently aligned with the length of a passage 118 so that the fish will fall between adjacent bars 117.

The bottoms of the passageways 119a, 119b, 119c and 119d are roughened for cooperation with the sides of scaled fish as the upper frame 134 in which the passageways are formed is reciprocated in the direction indicated by the arrows in FIG. 26 relative to the lower supporting frame 134'. Such reciprocation will cause the roughened surface to shift fish lengthwise headfirst toward the convergent ends of the passageways 120a to 120d', inclusive, and the discharge chutes 121a to 121d', inclusive. In addition, the bottoms of all of the sorting troughs 122a to 122d', inclusive, have serrations 135 extending transversely of their lengths and raked toward their discharge ends 129a to 129d', respectively. The reciprocation of the upper frame 134 will cause such serrations to feed fish rapidly headfirst from the discharge chutes 121a to 121d', inclusive, to and past the fish sex-detecting stations.

The reciprocating movement of the upper frame 134 relative to the lower supporting frame 134' is accomplished by a rotating wobble plate plate 136 carried by rotating shaft 137. The periphery of the wobble plate is received between two rollers 138 mounted in brackets 139 depending from the upper frame 134. The thrust of the wobble plate in opposite directions transmitted to the upper frame 134 is supplemented by the force of springs 140 each having one end attached to the lower frame 134' and having its opposite end secured to a bar 141 of the upper frame.

The shaft 137 is supported by bearings 142 and carries a drive pulley 143 that is connected to the drive pulley of a motor 144 by a v-belt 145. When the upper frame 134 is in a central position relative to the lower frame 134' the two springs 140 may be unstressed, or at least will be equally stressed. As the wobble plate is turned to move the upper frame in one direction relative to the lower frame one of the springs 140 will be stressed so that, when the wobble plate moves into a position for return movement of the upper frame 134 relative to the lower frame 134', any thrust exerted by the wobble plate on a roller 138 will be supplemented by the force of the stressed spring 140.

As rotation of the wobble plate 136 moves the frame 134 to the other side of its central position the other spring 140 will be stressed so that, when the wobble plate has effected full movement of the frame in such opposite direction, the second spring 140 thus stressed will supplement the action of the wobble plate to assist in moving the frame 134 back again toward central position. This cycle of operation will continue with the upper frame moving alternately first in one direction and then in the opposite direction from a central or neutral position so as to effect reciprocation of the upper frame section. Such reciprocation will, in the manner described above, cause fish supported by bars 117 to swing into positions generally parallel to such bars for dropping between them to the passageways 119a to 119d, will effect movement of each fish headfirst along such a passageway to one end or the other and finally will effect headfirst movement of the fish along the sorting troughs 122a to 122d'.

Although some fish will be moving headfirst in passgeways 119a to 119d to the left as seen in FIGS. 24, 25 and 26, the discharge chutes 121a', 121b', 121c' and 121d' reverse the direction of movement of the fish so that upon discharge from such chutes the fish will be moving headfirst in the opposite direction, that is to the right, along sorting troughs 122a', 122b', 122c' and 122d'. Consequently, all of the discharge chutes 121a to 121d', inclusive, will discharge the fish into the sorting troughs headfirst moving in the direction from left to right, as seen in FIGS. 24 to 27, inclusive.

When no fish are passing through the sex-detecting stations the radiant energy from the sources 61 passing through the transparent portions 60 of the sorting troughs will be projected at maximum intensity onto the radiant-energy responsive devices 62' and 63'. When a female fish passes between a radiant energy source and the radiant-energy responsive devices, the amount of radiant energy absorbed will be much less than that absorbed by a male fish. The energy-responsive devices 62' and 63' are connected to the actuators 128a to 128d', inclusive, so that an actuator will not be actuated to swing a gate from a full line position shown in FIG. 25 to a broken line inclined position of that figure unless the radiant transmission from the corresponding radiant energy source to the associated energy-responsive devices is decreased by an amount greater than the reduction that would be effected by passage of a female fish between such radiant-energy source and such energy-responsive devices.

Consequently, the gates 126a to 126d' will not be swung to shunt femal fish out of the sorting troughs, and such fish will be discharged from the trough ends 129a to 129d', inclusive, onto the conveyor 133, whereas the actuators 128a to 128d' will be actuated to swing the gates 126a to 126d' into the inclined positions shown in broken lines in FIG. 25 to shunt male fish through the openings 130a to 130d', inclusive, so as to fall through the upright passages 131a to 131e into the conveyor 132. By this procedure, the male fish and the female fish will be separated automatically with the male fish being carried away by the conveyor 132 and the female fish being carried away by the conveyor 133.

In the fish-sorting apparatus shown in FIGS. 29 and 30 the fish are dumped into the supply hopper 114' from which fish are removed by bucket elevators 115a and 115*b* having a space 146 between them. The fish are deflected to one side or the other of this space by a saddleback 147 to place the fish in position to be picked up by the bucket elevators 115*a* and 115*b*. From elevator 115*a* the fish are dumped into one or the other of the supply chutes 148*a* and 148*b*. Correspondingly, the bucket elevator 115*b* dumps the fish into the supply chutes 148*c* and 148*d*.

From the supply chutes 148*a*, 148*b*, 148*c* and 148*d*, the fish are deposited on respective sections 149*a*, 149*b*, 149*c* and 149*d* of an initial orienting table. Fish are discharged from opposite ends of these sections, usually headfirst, onto corresponding sections 150*a*, 150*b*, 150*c* and 150*d* of a secondary orienting table. From the sections of this secondary orienting table, the fish are discharged headfirst into the various convergent wall sections 151*a*, 151*a'*, 151*b*, 151*b'*, 151*c*, 151*c'*, 151*d* and 151*d'*. By the time the fish reach the fish sex-detecting stations 152*a*, 152*a'*, 152*b*, 152*b'*, 152*c*, 152*c'*, 152*d* and 152*d'*, they are all moving headfirst in single file.

The apparatus of FIGS. 29 and 30 accomplishes the orienting and singling operation in a manner similar to that in which the apparatus shown in FIGS. 23 to 27 operates as described above. Through mechanism not shown in detail, the drive motor 144' driving belt 143' effects reciprocation of the upper frame 134*a* in the direction indicated by the arrow between the discharge ends of the chutes relative to the lower stationary frame 134*b*. The surfaces of the initial orienting table and of the secondary orienting table are roughened so that the reciprocation will cause the fish to move until they are oriented headfirst toward one side of the apparatus or the other. For this purpose, the fish can pass freely under the upper initial orienting table composed of sections 149*a* to 149*d*.

The convergent sections 151*a* to 151*d'* have transverse serrations 137, as discussed in connection with the apparatus of FIGS. 23 to 27. These serrations are raked toward the respective sex-detecting stations 152*a* to 152*d'*, inclusive, so as to space the fish apart lengthwise by the time they reach the sex-detecting stations. The individual sex-detecting stations are similar in construction to that described in connection with FIGS. 27 and 28 except that the structure for separating the female fish and the male fish is somewhat different.

The device for separating the female fish and the male fish at each sex-detecting station includes a transfer trough section 153 swingably mounted on a pivot 153' to swing between a lower position for discharge of fish onto a conveyor 154 and an upper position for discharge of fish across bridge 155 to a conveyor 156. At the opposite side of the machine, the transfer trough sections can discharge fish onto the lower conveyor 154' or can be swung upward to discharge fish across bridge 155' to the upper conveyor 156'. The radiant-energy responsive devices at the fish sex-detecting stations are connected to control swinging of the transfer trough sections 153 so that female fish will be discharged onto one conveyor, such as conveyor 154 or conveyor 154', and male fish will be discharged onto the other conveyor such as across bridge 155 to conveyor 156 or across bridge 155' to conveyor 156'.

The apparatus shown in FIGS. 32 and 33 is similar to that shown and described in connection with FIGS. 29 and 30 except that the transfer mechanism shown in detail in FIG. 33 is substituted for the transfer mechanism shown in detail in FIG. 31. Also, instead of having only four convergent sections at each side of the apparatus, as shown in FIG. 29, the apparatus of FIG. 32 has eight convergent discharge sections leading to eight fish sex-detecting stations, respectively. As in the apparatus of FIG. 29, the apparatus of FIG. 32 includes an initial orienting table having sections 149*a*, 149*b*, 149*c* and 149*d* to which fish are supplied from supply chutes, such as 148*a* and 148*b*, respectively. From the initial orienting table the fish are deposited into the corresponding sections of the lower secondary orienting table 150*a*, 150*b*, 150*c* and 150*d*.

From the secondary orienting table the fish are discharged headfirst at one side of the apparatus into convergent troughs 157*a* to 157*h*, respectively. Each trough has its respective sex-detecting station and transfer mechanism operated by the respective fish sex-detecting station to direct the fish either to a conveyor 158 or to a conveyor 159 depending upon the amount of radiant energy transmitted from the radiant-energy source to the radiant-energy responsive device at the particular station. A representative sex-detecting station and transfer device is shown in FIG. 32.

Each sex-detecting station has a pair of parallel gates 160 and 161 swingable in unison between a position communicating with a passage 162 leading to belt 158 and a bridge passage 163 leading across belt 158 to belt 159. The gates will be swung in response to the amount of radiant energy received by the energy-responsive device of the particular sex-detecting station so that either the fish will be directed by the gates 160 and 161 through the passage 162 to the belt 158, or will be directed through the bridge passage 163 to the belt 159. Again, therefore, fish of one sex will be discharged to conveyor 158 and fish of the other sex will be discharged to conveyor 159.

In the foregoing description, reference has been made to the detector as including a radiant-energy source energy from which will be received by a energy-responsive element. While various types of radiant energy can be used in the apparatus and process described, including visible light, it is preferred that the radiant-energy source generate infrared radiation and that the energy-responsive elements be responsive to the reception of infrared radiation. Use of infrared radiation is preferred because the energy-responsive element can be selected to respond only to infrared radiation and not to light radiation. The testing and sorting operation can, therefore, be conducted under daylight conditions or artificial light conditions of any intensity without danger of such light activating the energy-responsive element to give a false indication of a fish characteristic. Moreover the difference between the amount of infrared radiation transmitted by a female fish and that transmitted by a male fish is greater than the difference between the amount of light transmitted by a female fish and that transmitted by a male fish, so that the infrared testing mechanism is more sensitive.

We claim:

1. Apparatus for sorting fish including detector means for detecting a characteristic of fish, fish-moving means for moving fish past the detector means, and channeling means operable in response to the detector means to channel fish in accordance with the effect of the fish on the detector means, the improvement comprising the fish-moving means including fish-orienting and fish-singling means spaced a substantial distance from the detector means for orienting fish in disarray for lengthwise movement headfirst in single file, and substantially horizontal fish-accelerating means between said fish orienting and fish-singling means and the detector means for accelerating the fish in single file to space them apart prior to their movement past the detector means.

2. The apparatus defined in claim 1, in which the fish-accelerating means include movable pusher means engageable with a side of a fish.

3. The apparatus defined in claim 1, in which the fish-accelerating means include tooth means engageable, respectively, with opposite sides of a fish, and means for moving at least one of said tooth means longitudinally of the fish.

4. The apparatus defined in claim 1, in which the fish-accelerating mans includes rotating brush means engageablewith a side of a fish.

5. The apparatus defined in claim 1, in which the fish-accelerating means includes rotating brush means engageable with opposite sides of the fish, said brush means engaging one side of the fish rotating oppositely to brush means engaging the opposite side of the fish.

6. Apparatus for sorting fish including detector means for detecting a characteristic of fish, fish-moving means for moving fish past the detector means, and channeling means operable in response to the detector means to channel fish in accordance with the effect of the fish on the detector means, the improvement comprising fish-moving means including an arcuate trough of truncated crescent shape having end portions of a width slightly greater than the maximum width of a fish being processed in the apparatus, said arcuate trough having a rough surface on which the fish lie, and oscillating means for oscillating said trough for effecting movement of fish along the trough by the action of such rough surface.

7. The apparatus defined in claim 6, in which the arcuate trough is supported by first spring means attached to the trough and by second spring means detached from the trough, and drive means for deflecting said first spring means relative to said second spring means.

8. The apparatus defined in claim 7, and weight means connected to movement with the second spring means.

9. The apparatus defined in claim 7, in which the drive means includes rotary wedging means interposed between the first spring means and the second spring means.

10. The apparatus defined in claim 9, in which the rotary wedging means includes an axle and two disks inclined relative to each other and mounted on said axle.

11. The apparatus defined in claim 6, in which the arcuate trough includes a first fish-supporting portion spaced from an end of the arcuate trough and elevated above a second fish-supporting portion onto which fish may drop from said first fish-supporting portion, for providing a fish passage beneath said first fish-supporting portion.

12. Apparatus for sorting fish including detector means for detecting a characteristic of fish, fish-moving means for moving fish along a path past the detector means and channeling means operable in response to the detector means to channel fish in accordance with the effects of the fish on the detector means, the detector means including a radiant-energy source at one side of such path and energy-responsive means at the opposite side of such path, the improvement comprising the energy-responsive means including a first energy-responsive element generally centered with respect to such path and two additional energy-responsive elements spaced lengthwise of the path from said first energy-responsive element, spaced apart transversely of such path and located at opposite sides of said first energy-responsive element with respect to such path and having no energy-responsive elements therebetween, whereby the orientation of the back and belly of a fish relative to the path is detected.

13. The apparatus defined in claim 12, in which the radiant-energy source transmits infrared energy and the energy-responsive means is responsive to such infrared energy.

14. In conveying means for fish including pushing means and means for reciprocating said pushing means, the improvement comprising the pushing means including plate means having a plurality of pushing teeth integral with and upstanding from said plate means, made of the same material as said plate means and inclined from said plate means in one direction for producing a pushing force on a fish while being moved in one direction greater than the force exerted by said teeth on the fish when said pushing means is moved in the opposite direction.

15. The apparatus defined in claim 14, in which the pushing means are engageable with one side of the fish, and toothed means engageable with the opposite side of the fish having teeth similar to the teeth of the pushing means.

16. In apparatus for detecting a characteristic of fish including a radiant-energy source for location at one side of a fish directed toward the fish and energy-responsive means for location at the other side of the fish for receiving from the fish energy originated by the radiant-energy source, the improvement comprising fish-characteristic indicating signal light means, and actuating means operable by the energy-responsive means for controlling illumination of said signal light means for indicating a characteristic of a fish between the radiant-energy source and the energy-responsive means.

17. Apparatus for processing fish comprising fish-orienting means for orienting fish from a disarray condition into substantially unidirectional relationship, and fish-singling means for moving fish lengthwise headfirst along a substantially horizontal path in single file, including substantially horizontal fish-accelerating means for exerting a substantially horizontal accelerating force on fish moving in single file along such substantially horizontal path to space apart successive fish.

18. Apparatus for orienting fish from a disarray condition into a substantially parallel relationship comprising spaced parallel bars forming slots therebetween, the upper edges of said bars being saw-toothed with the teeth of alternate bars raked in the same direction and the teeth of the intermediate bars raked in the opposite direction, and means for vibrating said bars for effecting swinging of fish deposited on said bars in positions with their lengths extending crosswise of said bars into positions generally parallel to said bars to drop through the slots between said bars.

* * * * *

UNITED STATES PATENT OFFICE
CERTIFICATE OF CORRECTION

Patent No. 4,051,952          Dated October 4, 1977

Inventor(s) Edward G. Hauptmann and John Richard Green

It is certified that error appears in the above-identified patent and that said Letters Patent are hereby corrected as shown below:

Title page, [56] References Cited, after "Conway" insert --et al.--; then insert

--FOREIGN PATENT DOCUMENTS 1,454,209          2/1969          Germany

Column 3, lines 34 and 35, insert a period after "away" and cancel "taken on line 27--27 of FIG. 25."; line 38, cancel "27" and insert --25--

Column 16, line 67, cancel the comma after "file".

Column 17, line 14, cancel "mans" and insert --means--; line 15, cancel "engageablewith" and insert --engageable with--; line 42, cancel "to" and insert --for--.

Column 18, lines 10 and 11, cancel ", whereby the orientation of the back and belly of a fish relative to the path is detected".

Signed and Sealed this

Seventeenth Day of October 1978

[SEAL]

Attest:

RUTH C. MASON
Attesting Officer

DONALD W. BANNER
Commissioner of Patents and Trademarks